United States Patent [19]

Risby et al.

[11] 4,122,343
[45] * Oct. 24, 1978

[54] METHOD TO GENERATE CORRELATIVE DATA FROM VARIOUS PRODUCTS OF THERMAL DEGRADATION OF BIOLOGICAL SPECIMENS

[75] Inventors: Terence H. Risby, State College, Pa.; Alfred L. Yergey, III, Columbia, Md.

[73] Assignee: Chemetron Corporation, Chicago, Ill.

[*] Notice: The portion of the term of this patent subsequent to Feb. 21, 1995, has been disclaimed.

[21] Appl. No.: 777,366

[22] Filed: Mar. 14, 1977

Related U.S. Application Data

[63] Continuation-in-part of Ser. No. 682,781, May 3, 1976, Pat. No. 4,075,475.

[51] Int. Cl.$^2$ ...................... H01J 39/34; B01D 59/44
[52] U.S. Cl. .................................... 250/282; 250/288
[58] Field of Search ............... 250/281, 288, 282, 252, 250/423, 425

[56] References Cited

PUBLICATIONS

"Nonisothermal Kinetics Studies of the Hydrodesulfurization of Coal", Yergey, et al., I & EC Process Design & Development, vol. 13, pp. 233–240, Jul. 1974.
"Thermal Analysis – Mass Spectrometer Computer System and its Application to the Evolved Gas Analysis of Green River Shale & Lunar Soil Samples", Gibson, 23 Confer. on Anal., Chem. and Appl. Spectroscopy, 1972, pp. 243–255.

*Primary Examiner*—Alfred E. Smith
*Assistant Examiner*—B. C. Anderson
*Attorney, Agent, or Firm*—Vincent G. Gioia

[57] ABSTRACT

In a method generating correlative data from various products of thermal degradation of biological specimens and comprising sequential steps for each specimen of degrading such specimen by heating such specimen so as to cause various products of thermal degradation of such specimen to be evolved, ionizing the products of thermal degradation of such specimen by a technique causing negligible fragmentation, detecting ion currents for such specimen, and recording such detected ion currents, an improvement is attained wherein each specimen is heated in an identical non-isothermal time-dependent heating sequence, wherein a three-dimensional array comprising a large and sufficient number of ion currents, which correspond to substantially all detectible ratios of mass-to-charge within a range at a large and sufficient number of successive instants during the respective heating sequences, are detected and recorded for each specimen, and representative data from the three-dimensional array thus recorded for each one of such specimens are correlated to representative data from the three-dimensional array thus recorded for each other of the specimens. Therein, one dimension of each array represents ion currents, another dimension of such array represents mass-to-charge ratios, and another dimension of such array represents specimen temperatures.

10 Claims, 14 Drawing Figures

ION CURRENT INTENSITY
M/e
TIME (TEMP.)
DATA AXIS

ION CURRENT INTENSITY
M/e
TIME (TEMP.)
TOTAL ION PLOT

ION CURRENT INTENSITY
M/e
$t_1$
$t_2$
TIME (TEMP.)
SEQUENTIAL MASS SPECTRA

ION CURRENT INTENSITY
$m_1$ $m_2$ $m_3$
$t_1$
$t_2$
TIME (TEMP.)
SINGLE ION PLOT

METHOD TO GENERATE CORRELATIVE DATA FROM VARIOUS PRODUCTS OF THERMAL DEGRADATION OF BIOLOGICAL SPECIMENS

CROSS-REFERENCE TO RELATED APPLICATION

This application is a continuation-in-part of U.S. Ser. No. 682,781 which was filed May 3, 1976, which is assigned commonly with this application, and which is incorporated in its entirety in this application now U.S. Pat. No. 4,075,475.

BACKGROUND OF THE INVENTION

This invention pertains generally to mass spectrometry. This invention pertains particularly to a method employing mass spectrometry to generate correlative data from various products of thermal degradation of biological specimens so as to facilitate their classification and their identification.

Prior methods employing mass spectrometry to generate correlative data concerning biological specimens are discussed in two significant published references:

(1) H. L. C. Meuzelaar et al., "A Technique for Fast and Reproducible Fingerprinting of Bacteria by Pyrolysis Mass Spectrometry," *Analytical Chemistry*, Vol. 45, No. 3, March 1973, pages 587 et seq.;

(2) John P. Anhalt et al., "Identification of Bacteria Using Mass Spectrometry," *Analytical Chemistry*, Vol. 47, No. 2, February 1975, pages 219 et seq., also in:

(3) Henry L. Friedman et al.; a paper presented to the American Chemical Society, Second Western Regional Meetings, October 16-19, 1966 as summarized in *Chemical & Engineering News*, Sept. 5, 1966, *Thermochimica Acta* 1 (1970), pages 199 et seq. at 223-224; and *Thermal Analysis*, 1, (1969), pages 405 et seq. at 408-409.

Prior applications of mass spectrometry to other studies of related interest are discussed in three additional published references:

(4) Everett K. Gibson, Jr., et al., "Thermogravimetric-Quadrupole Mass-Spectrometric Analysis of Geochemical Samples," *Thermochimica Acta*, 4, (1972) pages 49 et seq.;

(5) Everett K. Gibson, Jr., "Thermal Analysis-Mass Spectrometer Computer System and its Application to the Evolved Gas Analysis of Green River Shale and Lunar Soil Samples," *Thermochimica Acta*, 5, (1973), pages 243 et seq.; and (6) Alfred L. Yergey et al., "Nonisothermal Kinetics Studies of the Hydrodesulfurization of Coal," *Industrial & Engineering Chemistry, Process Design & Development*, VOl. 13, July 1974, pages 233 et seq.

As described generally in references (1) and (2), prior methods to generate correlative data concerning bacterial specimens reflect such steps employing mass spectrometry for each specimen as degrading such specimen by heating such specimen so as to cause various products of thermal degradation of such specimen to be evolved, ionizing such products, detecting ion currents corresponding to different ratios of mass-to-charge among such products, and recording such detected ion currents. Referenct (2) describes a methodology wherein each specimen contained in a melting point capillary tube was introduced into a heated ion source operated at 300°-350° C. Reference (1) describes a methodology wherein ferromagnetic wires of Curie points of 510° C were used to heat a specimen. Reference (3) discloses unsatisfactory results, which are evident from the summary in *Thermal Analysis*.

Reference (1) suggests, at page 590, that ionization techniques causing negligible fragmentation such as field ionization, chemical ionization, or low-voltage electron-impact ionization may be useful. Further reference may be made to U.S. Pat. No. 3,555,272, which describes chemical ionization in substantial detail.

Reference (4) and reference (5) commonly disclose mass spectrometry as applied to monitor and identify released gases, whose spectra are known, from individual samples of geochemical substances. Reference (6) discloses kenetic studies of hydrogen sulfide, whose spectra are known, as evolved from non-isothermally heated coal.

Herein, the term "correlative" means susceptible to cross-correlation by known manual and automated techniques.

SUMMARY OF THE INVENTION

When bacterial specimens and other complex biological specimens are heated gradually, such specimens have been found to decompose in an orderly and reproducible manner, which has led to a substantially improved method for rapid identification of such specimens. The method also has been found to be useful to study both normal and leukemic lymphocytes and other white blood cells.

The method follows prior methods insofar as sequential steps for each specimen of degrading such specimen by heating such specimen so as to cause various products of thermal degradation of such specimen to be evolved, ionizing such products by a technique causing negligible fragmentation, detecting ion currents corresponding to different ratios of mass-to-charge among such products, and recording such detected ion currents for such specimen.

However, the method is improved wherein each specimen is heated in an identical non-isothermal time-dependent heating sequence, wherein a three-dimensional array comprising a large and sufficient number of ion currents, which correspond to substantially all detectible ratios of mass-to-charge within a range at a large and sufficient number of successive instants during the respective time-dependent heating sequences, are detected and recorded for each specimen, and wherein representative data from the three-dimensional array thus recorded for each one of such specimens are correlated to representative data from the three-dimensional array thus recorded for each other of such specimens.

One dimension of each three-dimensional array represents ion currents. Another dimension represents mass-to-charge ratios. Another dimension represents the specimen temperatures as a function of process time. Before any correlations are made, the data from each specimen preferably are reconstructed as representative two-dimensional arrays, wherein one dimension represents ion currents and another dimension represents specimen temperatures, for representative mass-to-charge ratios.

The method as thus improved has been successfully used to discriminate certain bacteria and certain lymphocytes, as explained below, and is expected to be generally useful to discriminate many types of biological organisms including bacteria, yeasts, molds, fungi, viruses, and unicellulars, as well as biological tissues including lymphocytes, leukocytes, phagocytes, erythrocytes, and platelets.

As an example of its utility, correlative data of ion current versus time-temperature have been successfully used to differentiate individual species (*Arthrobacter oxydans* and *Arthrobacter globiformis* as actual examples) of a common bacterial genus at one mass-to-charge ratio (m/e 549 in such examples), which appears to represent characteristic differences for such species, although plural ratios may have to be studied for successful differentiation of other specimens.

The foregoing and other objects, features, and advantages of this invention are made evident in the descriptions below of exemplary modes to carry out this invention, with the aid of the several accompanying drawings.

DETAILED DESCRIPTION OF EXEMPLARY MODES

Figure 1:
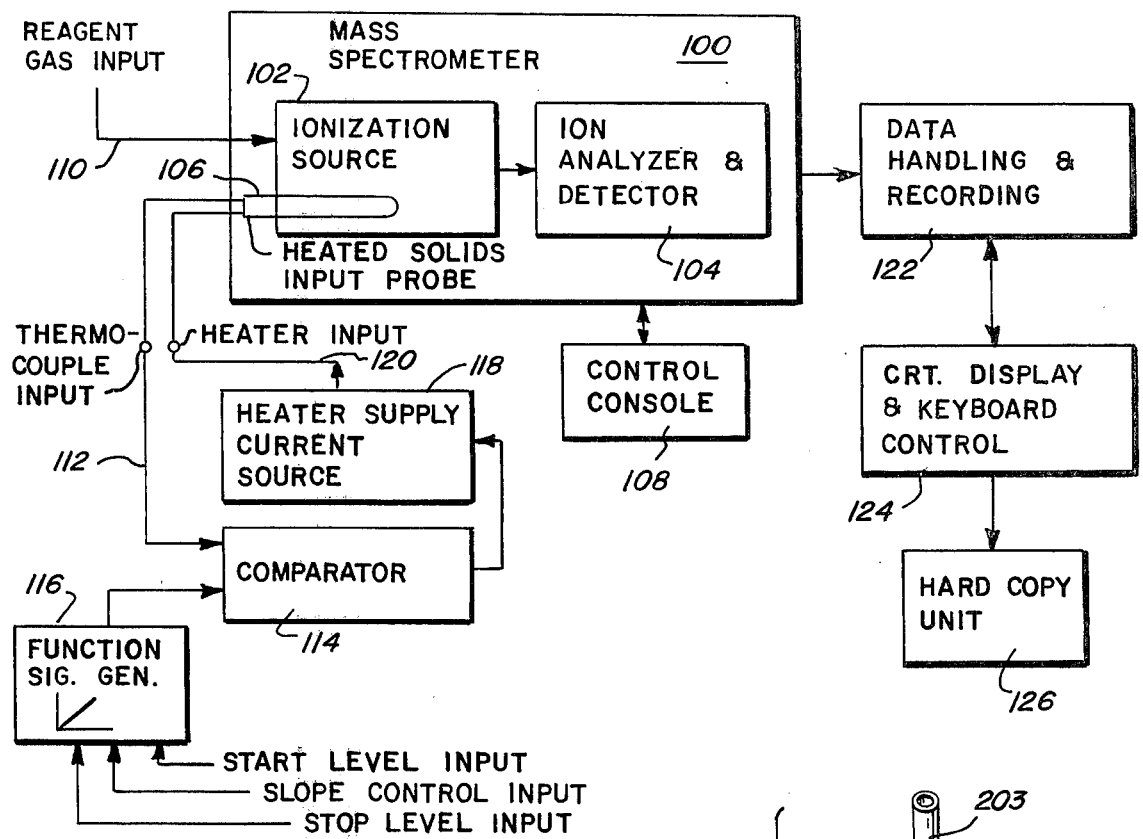
FIG. 1 is a schematic-block diagram of a typical arrangement of conventional apparatus which may be used in practicing this invention.

FIG. 1 shows, in block diagram, one arrangement of conventional apparatus that may be used to practice the substantially improved method of this invention. The apparatus includes a quadrupole mass spectrometer 100, preferably a BIOSPECT chemical ionization mass spectrometer commercially available formerly from Scientific Research Instruments Corporation of Baltimore, Md., and presently from its successor, Chemetron Corporation, Medical Products Division, which has a chemical ionization source 102, an ion analyzer-detector 104, and a heated solids probe 106 adapted to heat a solid-phase sample. An electrical heater (not shown) is incorporated with the probe 106. The spectrometer 100 is associated with a conventional control console 108.

As required by any such chemical ionization mass spectrometers, which are characterized by negligible fragmentation of parent ions being ionized, a reagent gas input 110 is provided for a suitable reagent gas, which may be methane vapor, water vapor, or other reagents. In the preferred BIOSPECT spectrometer, such gas is directed internally of the source 102 to pass directly over the tip of the probe 106, so as to sweep molecular fragments being produced directly from the tip of the probe 106 into a zone wherein such fragments are ionized within the source 102.

As shown in FIG. 1, a thermocouple output line 112 from the probe 106 is presented as one input to a comparator 114, and another input to the comparator 114 is provided by a function signal generator 116. Thus, the temperature of the probe 106 is compared with a time-dependent function, which is predetermined and non-isothermal and preferably is a linear ramp function, and any deviation causes an output from the comparator 114 to a supply 118 of electrical energy to the heater (not shown) so as to cause an increased or decreased supply of electrical energy to the heater as necessary to cause the temperature of the probe 106 and thus the temperature of a sample carried by the probe 106 to track the function provided by the generator 116.

The electrical output signals from the spectrometer are presented to a conventional recording system 122, which is controlled by a conventional keyboard unit 124, so as to record selected data corresponding to the analyzed and detected ions. The unit 124 may be associated with a cathode-ray-tube display unit and a hard-copy unit 126. Suitable equipment is commercially available from Systems Industries of Sunnyvale, Calif., and also from Hewlett-Packard and from the Kerns Group.

Figure 2:
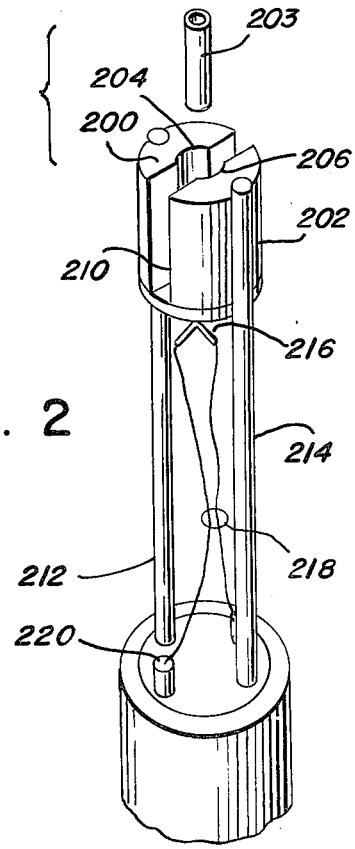
FIG. 2 is a perspective view of a special heated solids probe tip which may be used with this invention in the apparatus of FIG. 1.
Figure 3:
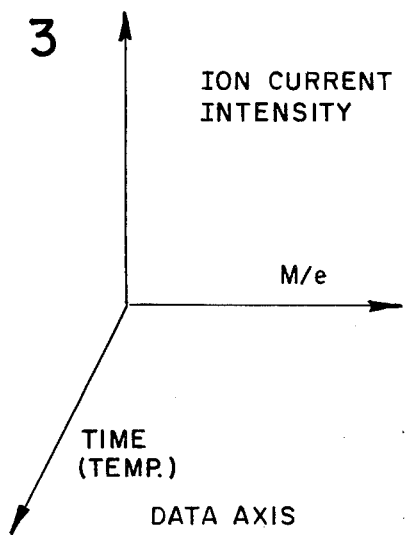
FIGS. 3, 4, 5, and 6 are graphical depictions of typical data which may result from this invention and of possible utilization of such data to facilitate classification and identification of biological specimens.
Figure 4:
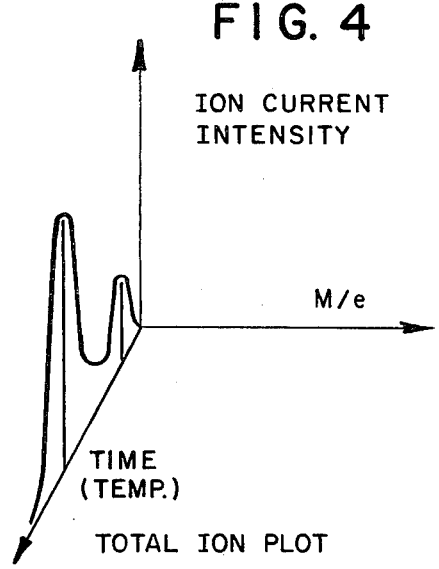
Figure 5:
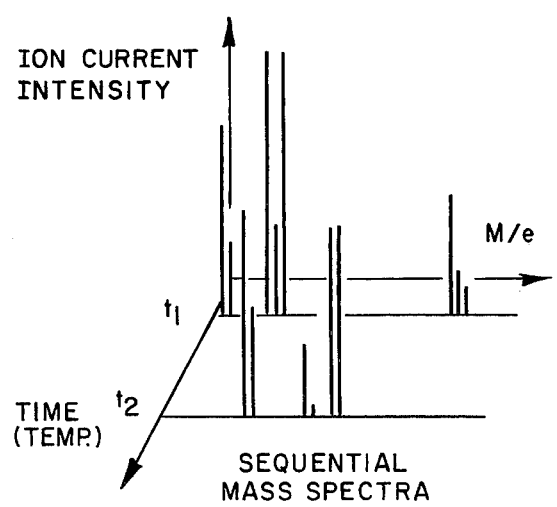
Figure 6:
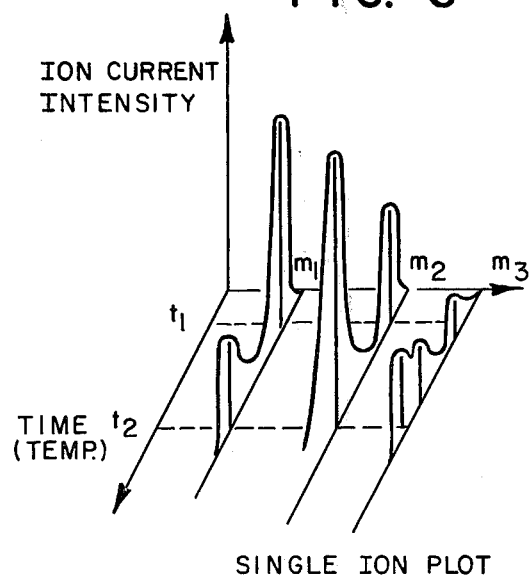
Figure 7:
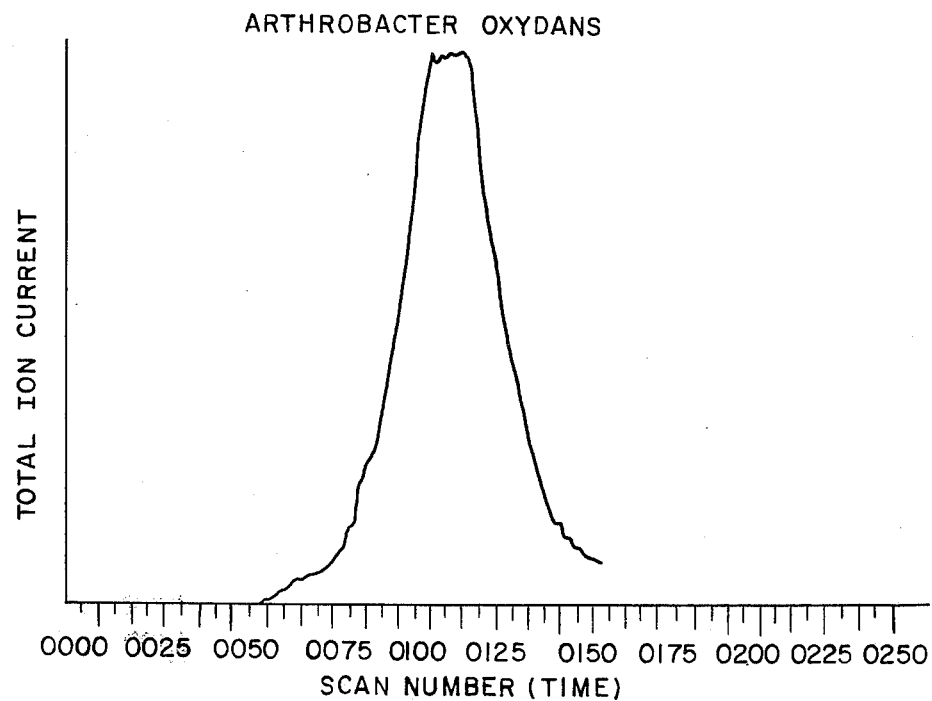
FIGS. 7 through 10 depict the total ion current versus time or temperature and one exemplary ion mass spectrum taken at a time corresponding to the leading edge portion of the total ion plot for two particular types of bacteria in a process according to this invention.
Figure 8:
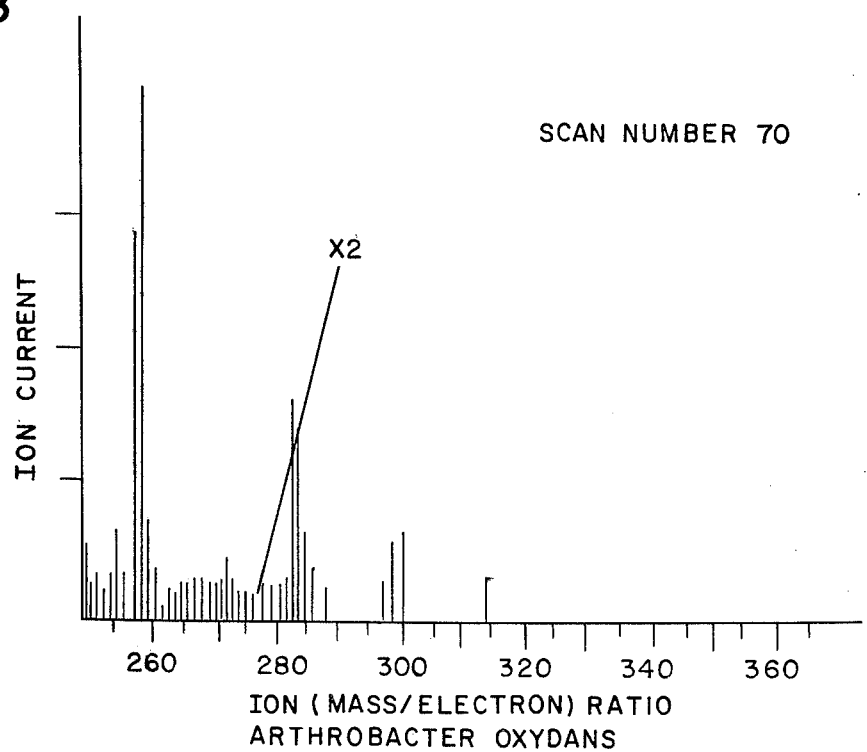
Figure 9:
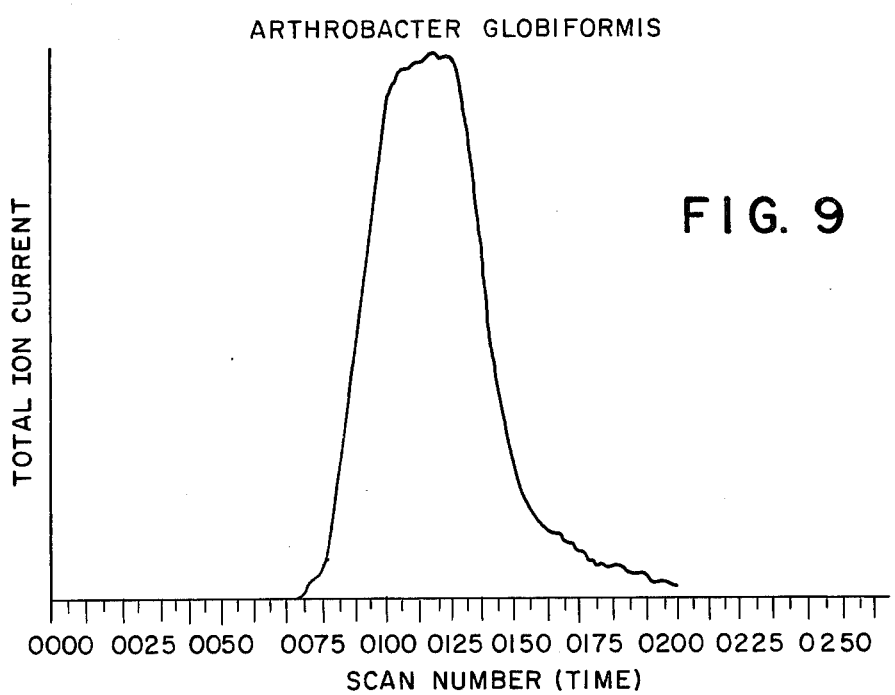
Figure 10:
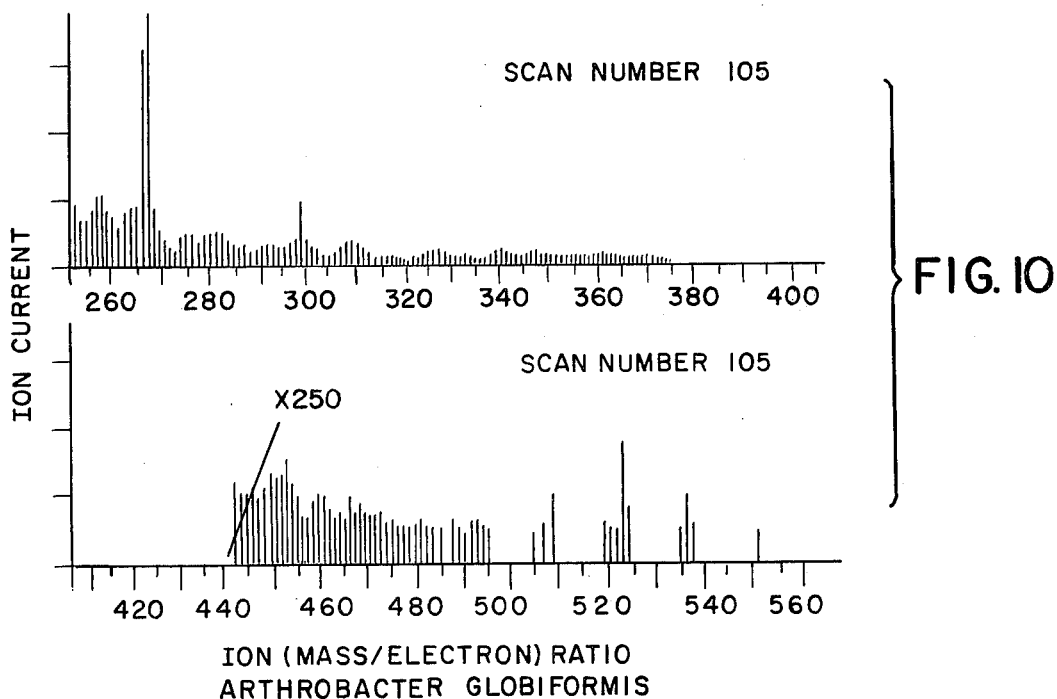
Figure 11:
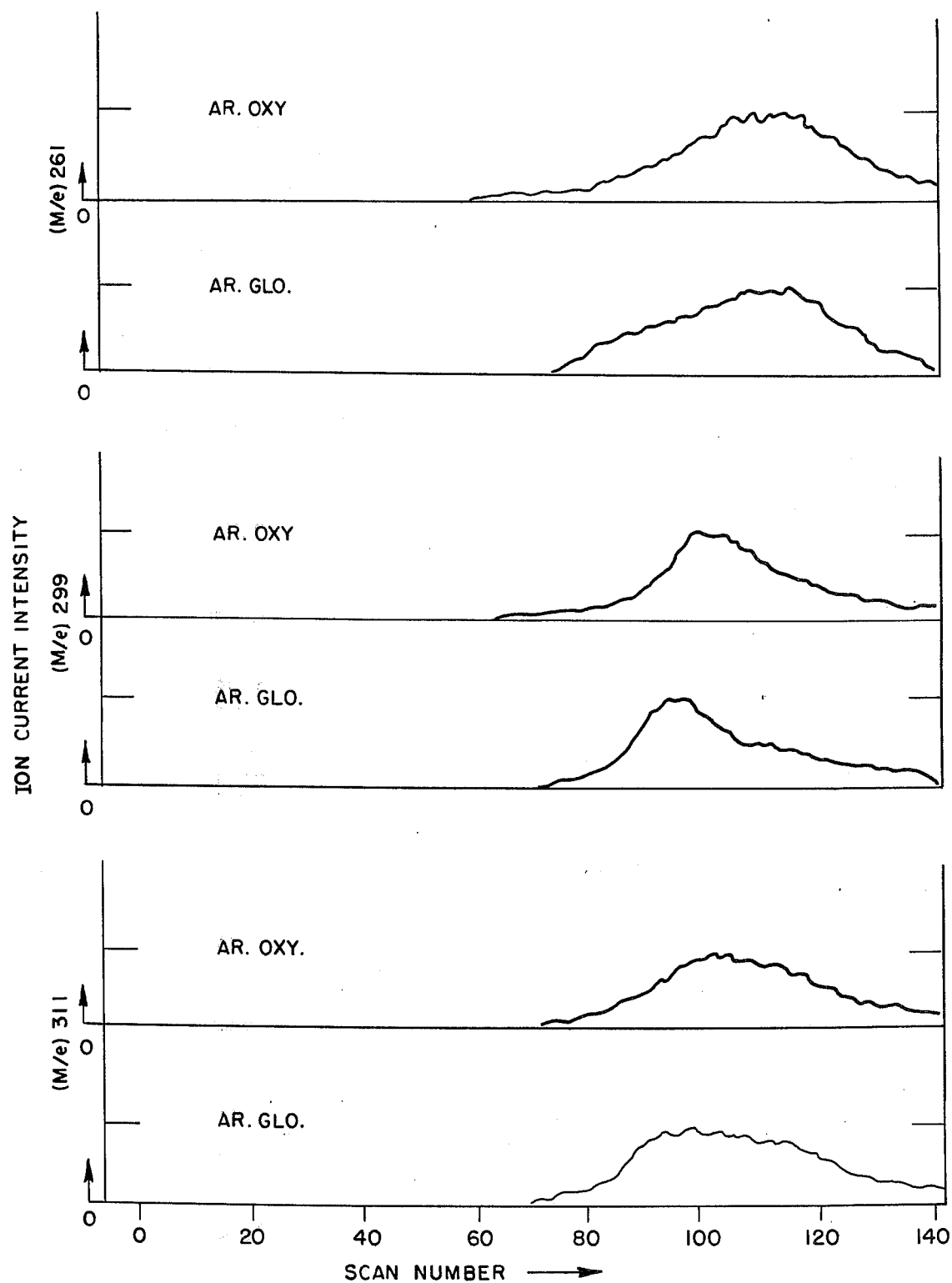
FIGS. 11 and 12 are plots of relative ion intensity versus time or temperature for various specific ion masses for each of the two types of bacteria utilized and referenced in FIGS. 7 through 10.
Figure 12:
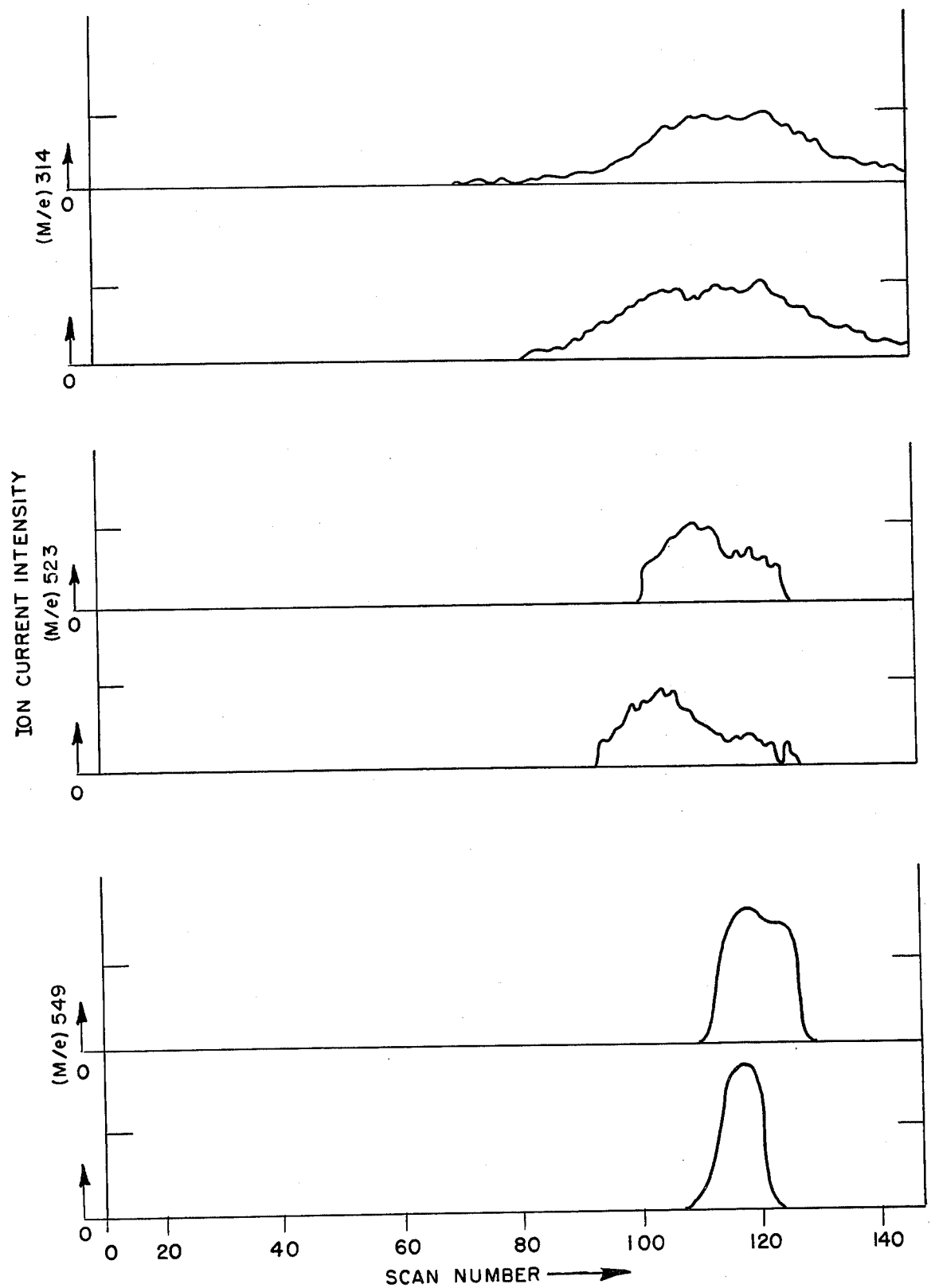

An alternative to the aforesaid probe is shown in FIG. 2 to comprise two half-cylinders 200 and 202 (preferably formed of stainless steel) having mating semi-circular recesses 204 and 206 forming a well to receive a small glass cylinder 203 containing a solid-phase sample. A disc 210, which preferably is made of kovar, is provided as a suitable heating element at a lower end portion of the cylinder 203. A thermocouple 216, which has electrical leads 218 communicating through suitable passages 220 in the probe, is spot welded to a central bottom portion of the disc 210. The leads 212 and 214, which also serve physically to position the tip of the probe, preferably are formed of approximately 20 gauge stainless steel. In the preferred exemplary embodiment, the tip has a diameter of approximately 0.156 inch, the slot has a height of approximately 0.175 inch and a width of approximately 0.132 inch and the disc or heating element has a thickness of approximately 0.0015 inch.

When either the arrangement of conventional apparatus of FIG. 1 or any other suitable apparatus are used to generate correlative data from various products of thermal degradation of biological specimens, known methodology is employed insofar as each specimen is heated and thus degraded so as to cause various products of thermal degradation of such specimen to be evolved, such products are ionized by a technique causing negligible fragmentation, ion currents corresponding to different mass-to-charge ratios among such products are detected, and such detected ion currents are recorded. However, these steps are substantially improved, as discussed below, by this invention wherein it does not matter whether such products are known.

Each specimen is heated in an identical non-isothermal time-dependent sequence. A three-dimensional array comprising a large and sufficient number of ion currents, which correspond to substantially all detectible ratios of mass-to-charge within a range at a large and sufficient number of successive instants during the respective time-dependent heating sequences, are detected and recorded for each specimen. For each three-dimensional array, one dimension represents ion currents, another dimension represents mass-to-charge ratios, and another dimension represents specimen temperatures as a function of process time.

Herein, various references to a large and sufficient number of ion currents at a large and sufficient number of successive instants means that a sufficiently large number of discrete data are detected and recorded that a surface may be visualized when the data are plotted in convenient coordinates. Actually, such a visualized surface is illusory, for no reason to allow the data to be interpolated is seen.

Representative data from the three-dimensional array thus recorded for each one of such specimens are correlated to representative data from the three-dimensional array thus recorded for each other of such specimens. Before any correlations are made, the data from each specimen may conveniently be reconstructed as representative two-dimensional arrays, wherein one dimension represents ion currents and another dimension represents specimen temperatures for representative mass-to-charge ratios.

When the specimens are bacterial specimens, it has been found advantageous for specimen temperature to be varied from ambient temperature to approximately 400° C at a gradient of 20° C per minute, and for 8.3 second scans to be made within a range of detected mass-to-charge ratios from approximately 250 atomic mass units to approximately 750 atomic mass units. Approximately 75,000 data may thus be collected and displayed in various arrays that maybe analyzed to find characteristic plots for particular bacteria.

For simplified initial approximation, it has been found advantageous to display such two-dimensional arrays for each specimen, at different mass-to-charge ratios, whereby those arrays that may be posited as characteristic may be visually isolated, and correlating representative data from such arrays for respective specimens by known techniques (linear correlation as an example) at confidence levels appropriate for the volume of collected data for each specimen. For full implementation, computerized pattern-recognition techniques and other highly sophisticated techniques may be warranted.

It has been demonstrated, by actual experimentation with the substantially improved method of this invention, that individual species of a common bacterial genus exhibit both common and dissimilar spectra in different ranges, that the genus may thus be fingerprinted for replicate identifications, and that individual species may thus be differentiated from one another within the genus. Comparable results were obtained for both normal and leukemic lymphocytes.

EXAMPLE 1

Five genera of bacteria, representing a diverse group of organisms, were studied. There were also related types, as the group also included two strains each of two species.

TABLE 1

| Organism | ATCC no. | Sequence |
| --- | --- | --- |
| Pseudomonas putida | 12633 | A |
| Pseudomonas putida | 15073 | B |
| Pseudomonas fluorenscens | 13525 | C |
| Escherichia coli | 4147 | D |
| Escherichia coli | 11775 | E |
| Bacillus megaterium | 14581 | F |
| Bacillus subtilis | 6051 | G |
| Arthrobacter oxydans | 14358 | H |
| Arthrobacter Globiformis | 8010 | I |

TABLE 1-continued

| Organism | ATCC no. | Sequence |
| --- | --- | --- |
| Arthrobacter amylovora | 15580 | J |

Table 1 lists ten organisms obtained from American Type Culture Collection (ATCC), Rockville, Md., along with the accession number of each organism. These ten organisms were prepared at the ATCC by using a 10% inoculation of 250-ml nutrient broth, culturing for 24 h, harvesting the organisms, spinning down the cells, washing in 0.1 M Phosphate buffer, and lyopholyzing for 18 h in two vials. Upon receipt, the vials were stored at 4° C. Samples for analysis were prepared by opening a sample vial, extracting a portion of dired cells with a flamed spatula, placing the cells onto a flamed watch glass, replugging the sample vial, placing the vial into a flamed test tube, and sealing the tube with a sterile gauze swatch. Only one sample vial was open in the room at a time, and all items in contact with the cells were flamed between openings.

The results showed not only that similar bacteria can be grouped together in terms of their overall decomposition patterns, but that they could be distinguished from each other. For example, *Arthrobacter oxydans* and *Arthrobacter globiformis* have similar plots at m/e 261, 299, 311, 314, and 523, but could clearly be distinguished by their differing plots at m/e 549. The method was even sensitive to differences between strains of the same species; one strain of *Escherichia coli* could be identified from its plot at m/e 314, another from its plot at m/e 523. Other studies indicated that such results were highly reproducible.

EXAMPLE II

In lymphocyte studies, white cells from leukemic patients and also from normal donors, when analyzed as described above, showed significant differences in their respective decomposition patterns. The findings suggest that the genetic and morphological differences seen in lymphocytes examined by other methods reflect the differences in molecular composition observed by the substantially improved method of this invention.

Figure 13:
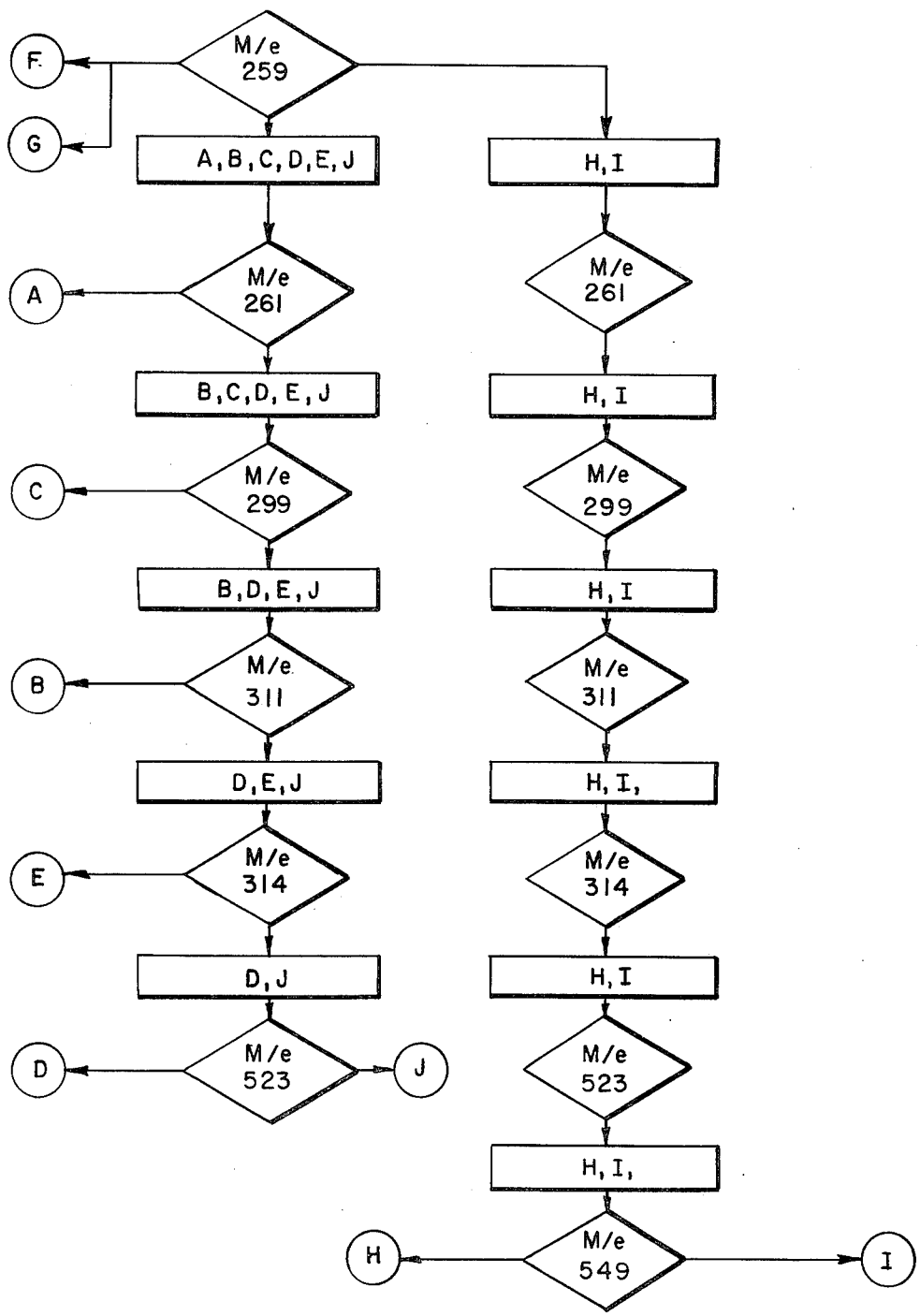
FIG. 13 is a schematic-block diagram of an exemplary sequence that may be utilized for processing the recorded data resulting from this invention and classifying and distinguishing an unknown bacteria.
Figure 14:
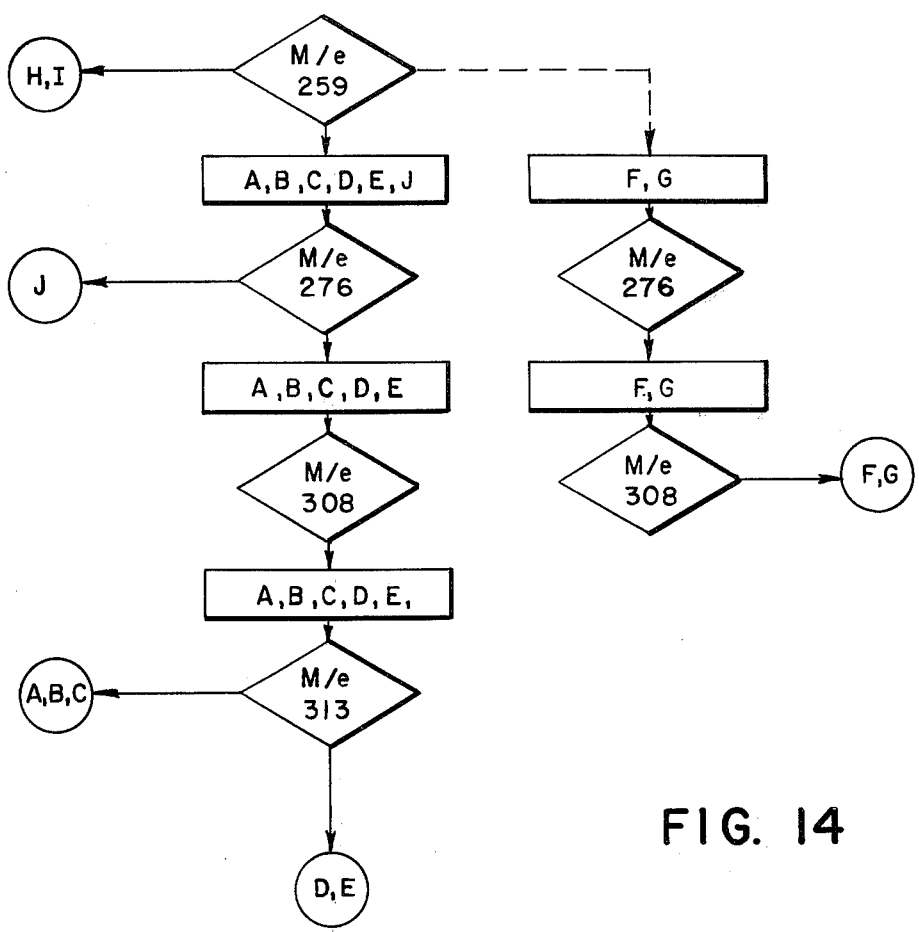
FIG. 14 is a schematic depiction of an exemplary sequence for grouping according to genus such types of bacteria giving rise to the data set forth in FIGS. 7 through 10.

In FIGS. 13 and 14, the diamonds represent points where separations occur, the organisms separated out appear in circles, and the organisms appearing in boxes are organisms unseparated.

FIG. 13 is an exemplary flow chart for differentiations. For the single ion plots at m/e 259, it is clear that organisms E and F are different from all the others present and from each other, organisms H and I are different from the remaining 6, but similar to each other, and that organisms A, B, C, D, E, and J resemble each other. For the single ion plot of m/e 261, it is clear that organism A is differentiated from B, C, D, E, and J, but no separation of H and I occurs. Those separated previously are no longer considered, but are carried on the chart for uniformity. For the single ion plot of m/e 299, organism C is separated, and so forth for the other plots. It is clear from the diagram that the organisms listed in Table 1 can be distinguished from each other.

It is also possible to classify or group the data into genera. FIG. 14 shows the flow chart for this grouping. The specific ion time or temperature profiles can be used to obtain a posteriori, the normal taxonomic relationships between the organisms. For the single ion plot of m/e 259, it is clear that organisms H and I are similar to each other and different from all others as found for the two representatives of genus Arthrobacter (this pairing is seen in most of the other single ion plots), organisms F and G are different from each other, but different in a rather specific way from the other six as well. Finally, organisms A, B, C, D, E, and J are all fairly similar. The plot for m/e 276 separates organism J from organisms A, B, C, D, and E (looking especially at the higher scan numbers) and is the representative of genus Erwinia. As found, m/e 308 shows the grouping for organisms F and G, the genus Bacillus organisms, m/e 313 shows that organisms D and E, genus Escherichia, are grouped thereby leaving the three organisms in genus Pseudomonas grouped by default. To summarize, Pseudomonas has a particular shape at m/e 257 that is shared by Escherichia and Erwinia, but is different at m/e 276, which groups Erwinia, and at m/e 313, which groups Escherichia.

Both the differentiation and grouping of FIGS. 13 and 14 are intended to show the operational principles of the pattern recognition techniques and are not meant to be limitive in the use of any particular mass number.

The substantially improved method of this invention is expected to be significant to the practice of clinical bacteriology. By classical methods, it can take from two days to three months to identify an organism. The substantially improved method of this invention may allow bacterial identification in less than twenty minutes after a colony of cells have been taken from a suitable nutrient medium. It also may be easily adaptable to rapid identification of other organisms such as yeasts, molds, fungi, and viruses.

We claim:
1. In a method generating correlative data from various products, either known or unknown products, of thermal degradation of biological specimens and comprising sequential steps for each specimen of:
 (a) degrading such specimen by heating such specimen so as to cause such products of thermal degradation of such specimen to be evolved;
 (b) ionizing such products of thermal degradation of such specimen by a technique causing negligible fragmentation;
 (c) detecting ion currents corresponding to different mass-to-charge ratios among the products of thermal degradation of such specimen, and
 (d) recording such detected ion currents for such specimen;
as improvement wherein:
 (e) each specimen is heated in an identical non-isothermal time-dependent heating sequence;
 (f) a three-dimensional array comprising a large and sufficient number of ion currents, which correspond to substantially all detectible ratios of mass-to-charge within a range at a large and sufficient number of successive instants during the respective time-dependent heating sequences, are detected and recorded for each specimen,
wherein one dimension of each three-dimensional array represents ion currents, another dimension of such three-dimensional array represents mass-to-charge ratios, and another dimension of such three-dimensional array represents specimen temperatures as a function of process time; and
 (g) representative data from the three-dimensional array thus recorded for each one of such specimens are correlated to representative data from the three-dimensional array thus recorded for each other of such specimens.

2. The improvement of claim 1 wherein, before any correlations are made, the data from each specimen are made, the data from each specimen are reconstructed as representative two-dimensional arrays, wherein one dimension represents ion currents and another dimension represents specimen temperatures, for representative mass-to-charge ratios.

3. The improvement of claim 2 wherein the specimens are bacteria.

4. The improvement of claim 3 wherein the range of detected mass-to-charge ratios extends from approximately 250 atomic mass units to approximately 750 atomic mass units.

5. The improvement of claim 2 wherein the specimens are lymphocytes.

6. The improvement of claim 1 wherein the specimens are from a subgroup of a group of biological organisms consisting essentially of these subgroups: (i) bacteria; (ii) yeasts; (iii) molds; (iv) fungi; (v) viruses; and (vi) unicellulars.

7. The improvement of claim 1 wherein the specimens are from a subgroup of a group of biological tissues consisting essentially of the subgroups: (i) lymphocytes; (ii) leukocytes; (iii) phagocytes; (iv) erythrocytes; and (v) platelets.

8. The improvement of claim 1 wherein the range of detected mass-to-charge ratios extends from approximately 250 atomic mass units to 750 atomic mass units.

9. The improvement of claim 1 wherein the data from some specimens are reference data.

10. The improvement of claim 1 wherein the total ion current as a function of the temperature of the specimen also is detected and recorded for each one of the specimens and also is correlated to the total ion current detected and recorded in like manner for each other of the specimens.

* * * * *